(12) United States Patent
Schäffler-Wachter et al.

(10) Patent No.: US 6,402,752 B2
(45) Date of Patent: Jun. 11, 2002

(54) POLYAXIAL PEDICLE-SCREW

(75) Inventors: Martin Schäffler-Wachter, Neu-Ulm; Helmut Schönhoffer, Erbach, both of (DE)

(73) Assignee: Ulrich GmbH & Co. KG, Ulm (DE)

( * ) Notice: Subject to any disclaimer, the term of this patent is extended or adjusted under 35 U.S.C. 154(b) by 0 days.

(21) Appl. No.: 09/778,336

(22) Filed: Feb. 7, 2001

(30) Foreign Application Priority Data

Feb. 7, 2000 (DE) .......................... 100 05 385

(51) Int. Cl.⁷ .............................. A61B 17/56
(52) U.S. Cl. .................. 606/61; 606/72; 606/73
(58) Field of Search .................. 606/61, 60, 53, 606/86, 72, 73; 623/17.11, 17.15, 17.16

(56) References Cited

U.S. PATENT DOCUMENTS

| | | | | |
|---|---|---|---|---|
| 5,882,350 A | * | 3/1999 | Ralph et al. | 606/61 |
| 6,053,917 A | * | 4/2000 | Sherman et al. | 606/61 |
| 6,113,601 A | * | 9/2000 | Tatar | 606/61 |
| 6,139,549 A | * | 10/2000 | Keller | 606/61 |
| 6,280,442 B1 | * | 8/2001 | Barker et al. | 606/60 |

FOREIGN PATENT DOCUMENTS

| DE | 41 07 480 | | 9/1992 | |
|---|---|---|---|---|
| DE | 4107480 | * | 9/1992 | 606/61 |

* cited by examiner

*Primary Examiner*—Pedro Philogene
(74) *Attorney, Agent, or Firm*—Herbert Dubno; Andrew Wilford

(57) ABSTRACT

A pedicle-screw assembly has a screw extending along an axis and having a threaded shaft and a round head, an inner cap part carried on the head and swivelable on the head, and an outer cap part forming with the inner cap part a seat adapted to hold an end of a distraction/stabilizing rod. The outer cap part has formations engageable in a snap fit over the inner cap part, and an element on the outer cap part can be tightened to fix the rod in the seat. The outer cap part is generally U-shaped and formed with a base forming the seat and a pair of legs projecting parallel to the axis, flanking the cap inner part, and having ends engaged in a snap fit around sides of the cap inner part.

30 Claims, 6 Drawing Sheets

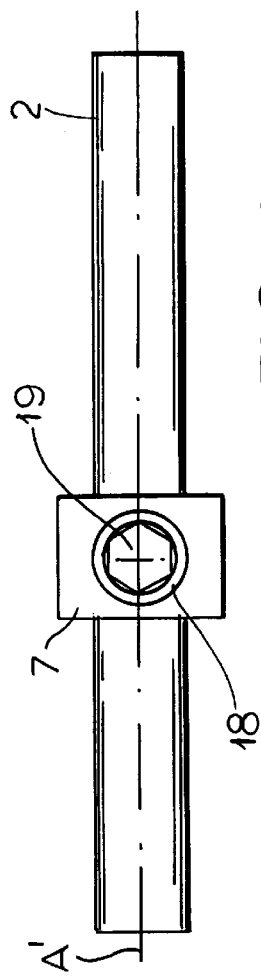
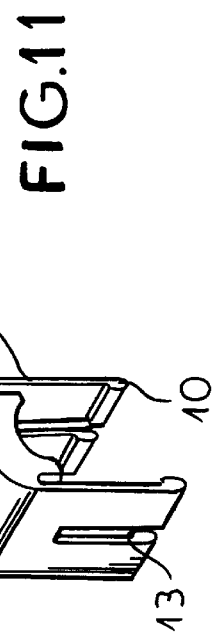
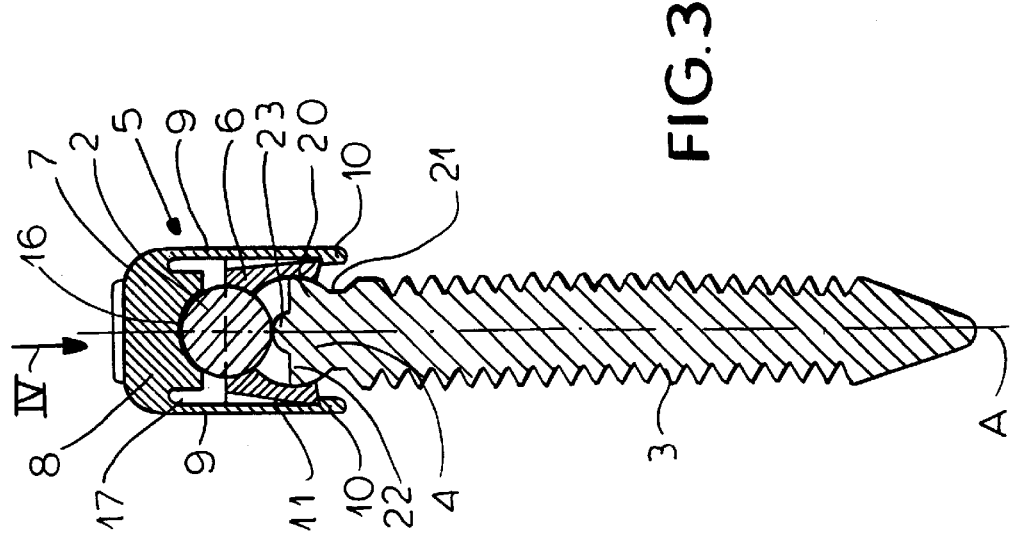

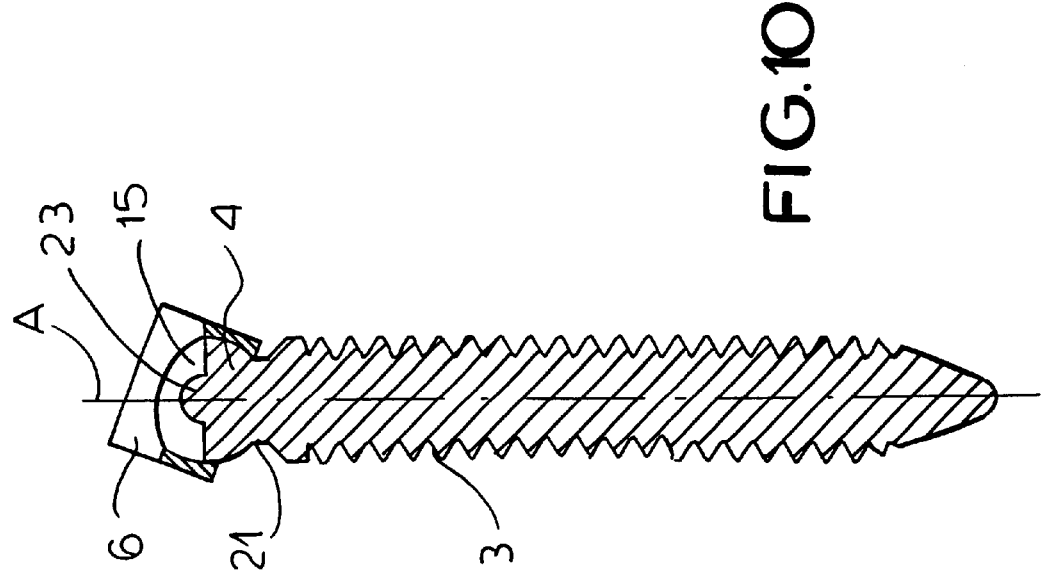
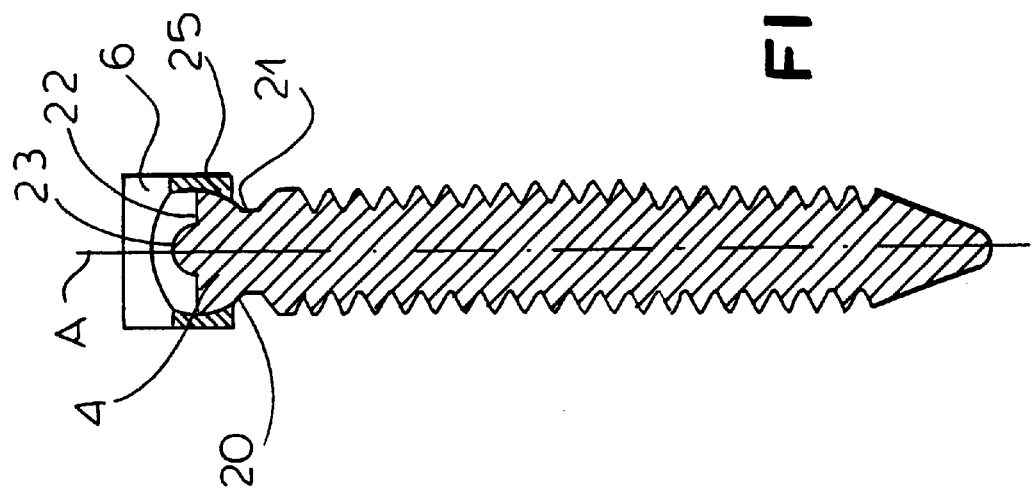

POLYAXIAL PEDICLE-SCREW

FIELD OF THE INVENTION

The present invention relates to a pedicle screw assembly.

BACKGROUND OF THE INVENTION

A standard pedicle screw assembly comprises a screw having an externally threaded stem having in turn a head provided with parts allowing it to be secured to one end of a distraction rod. Two such screws inserted into respective vertebrae are secured to such a rod to distract and/or stabilize a spinal column after, for instance, a disk operation.

In a standard such assembly as described in German patent document 4,107,480 the head of the screw has a pair of outwardly projecting parallel ridges with overhanging inner edges. A cap formed with a pair of complementary inwardly open slots that can fit with these ridges has a part-cylindrical recess forming with another part-cylindrical recess on the head of the screw a seat for the rod. The screw is threaded into the vertebrae, an end of the rod is fitted to its outer end, the cap is then slid transverse to the screw axis and parallel to the rod over the rod to capture it, and finally a screw threaded into the cap is tightened to press the rod down against the head of the screw and thereby fix the rod, cap, and screw together.

Since the cap of this system must be slid transversely onto the head of the screw, it is necessary to open the operating field sufficiently to allow such movement. This not only increases the extent of the surgery, but makes it impossible to install two such screws close to each other, for instance on adjacent vertebrae. Furthermore in most systems the actual position of the screw is critical as the rod can only be fitted to it in a limited range of positions.

OBJECTS OF THE INVENTION

It is therefore an object of the present invention to provide an improved pedicle screw.

Another object is the provision of such an improved pedicle screw which overcomes the above-given disadvantages, that is which can be installed in very close quarters.

SUMMARY OF THE INVENTION

A pedicle-screw assembly has according to the invention a screw extending along an axis and having a threaded shaft and a round head, an inner cap part carried on the head and swivelable on the head, and an outer cap part forming with the inner cap part a seat adapted to hold an end of a distraction/stabilizing rod. The outer cap part has formations engageable in a snap fit over the inner cap part, and an element on the outer cap part can be tightened to fix the rod in the seat.

With this system once the pedicle screws are set, the rod ends can be fitted to the inner cap parts which can be swiveled to accommodate any necessary angular offset. Then the outer cap parts are snapped in place and the assembly is tightened to lock the rod in place. The outer cap part does not have to be slid transversely into position but is moved normally generally axially as it is snapped over the inner cap part, so that little clearance is needed and the operating field does not have to be expanded to accommodate such movement.

The screw head according to the invention has an inner region with a part-spherical outer surface and an end face lying on a plane substantially perpendicular to the screw axis. The head is formed on the end face with a central part-spherical bump centered on the axis. In addition the outer cap part is generally U-shaped and formed with a base forming the seat and carrying the fixing means and a pair of legs projecting parallel to the axis, flanking the cap inner part, and having ends engaged around sides of the cap inner part. Each of the legs has an outer end that hooks under an edge of the respective side of the cap inner part. The outer cap part is formed parallel to and adjacent each leg with a groove so that lateral elastic deformation of the leg is increased.

Interengaging formations on the cap parts block movement of the cap parts relative to each other transverse to the axis. Furthermore, the outer and inner cap surfaces have confronting side faces. The interengaging formations include at least one axially extending ridge on one of the faces and a complementary axially extending slot on the face confronting the one face. The one face having the ridge is on the inner cap part although of course the reverse system would be usable.

The head and inner cap part have surfaces that engage each other and that are roughened. The fixing means is a screw threaded into the outer cap part and tightenable to pull the roughened surfaces of the inner cap part and head axially together. Thus when the assembly is tightened, the cap can no longer swivel on the screw.

The outer and inner cap parts are formed with confronting part-cylindrical concavities forming the seat. The inner cap-part concave seat half has a throughgoing aperture. The fixing screw presses the rod in the seat against the bump. To maximize the range of relative angular position the screw is formed at a base of the head with an annular inset so as to allow a wide range of swiveling of the cap on the head.

BRIEF DESCRIPTION OF THE DRAWING

The above and other objects, features, and advantages will become more readily apparent from the following description, reference being made to the accompanying drawing in which:

FIG. 3 is a section taken along line III—III of FIG. 2;

FIG. 4 is a top view taken in the direction of arrow IV of FIG. 3;

FIGS. 8 and 9 are sections taken along respective lines VIII—VIII and IX—IX of FIG. 7;

FIG. 10 is a view like FIG. 9 but with the inner cap part tipped; and

FIG. 11 is a perspective view from above of the outer cap part.

SPECIFIC DESCRIPTION

Figure 1:
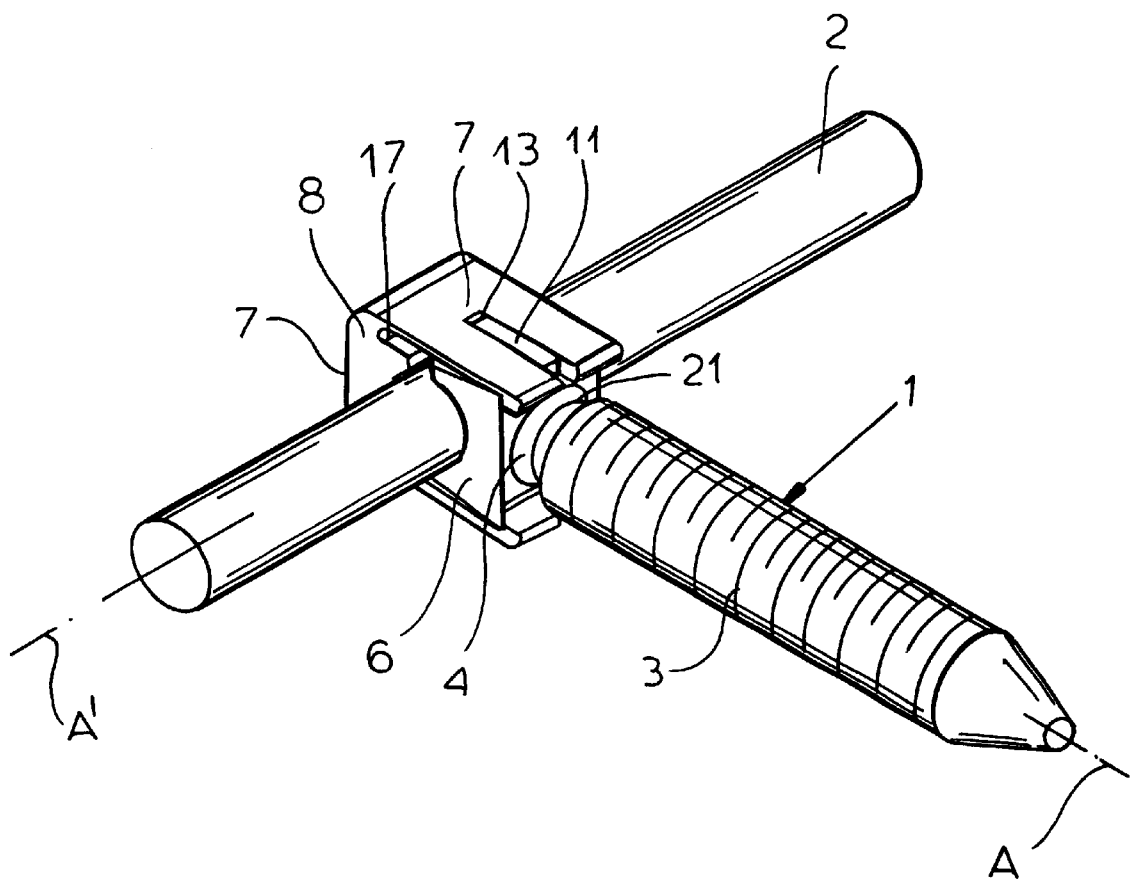
FIG. 1 is a perspective view of a pedicle-screw assembly according to the invention.
Figure 2:
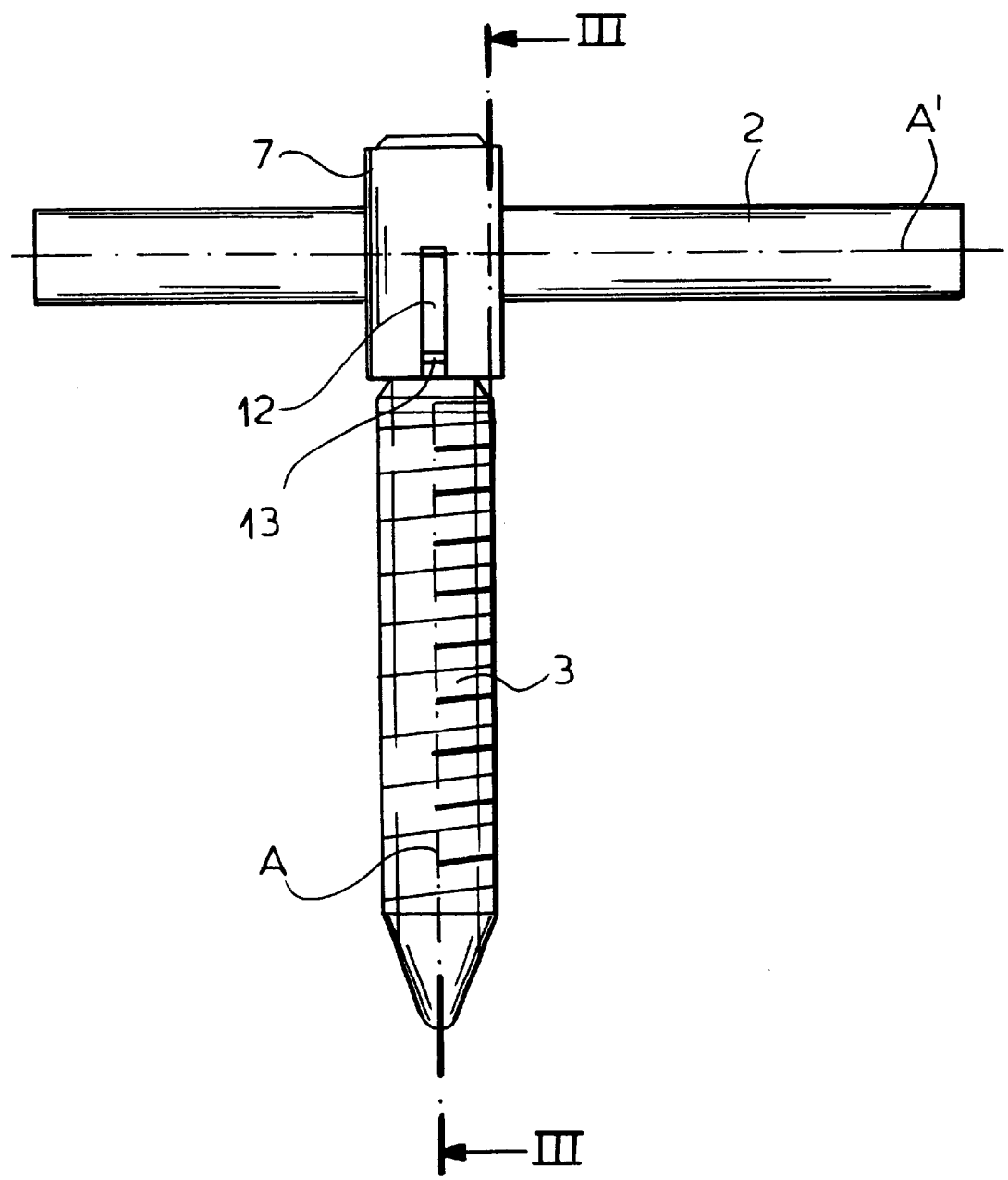
FIG. 2 is a side view of the assembly of FIG. 1.

As seen in FIGS. 1 through 4 a pedicle screw assembly basically comprises a screw 1 extending along an axis A and having a threaded stem 3 and a head 4 and a cap 5 adapted to clamp a distraction/stabilizing rod 2 extending along an axis A' crossing the axis A. Normally at least two such assemblies are used, with two screws 1 set in respective vertebrae and interconnected by a single rod 2 held in place on the screws 1 by their caps 5.

Figure 6:
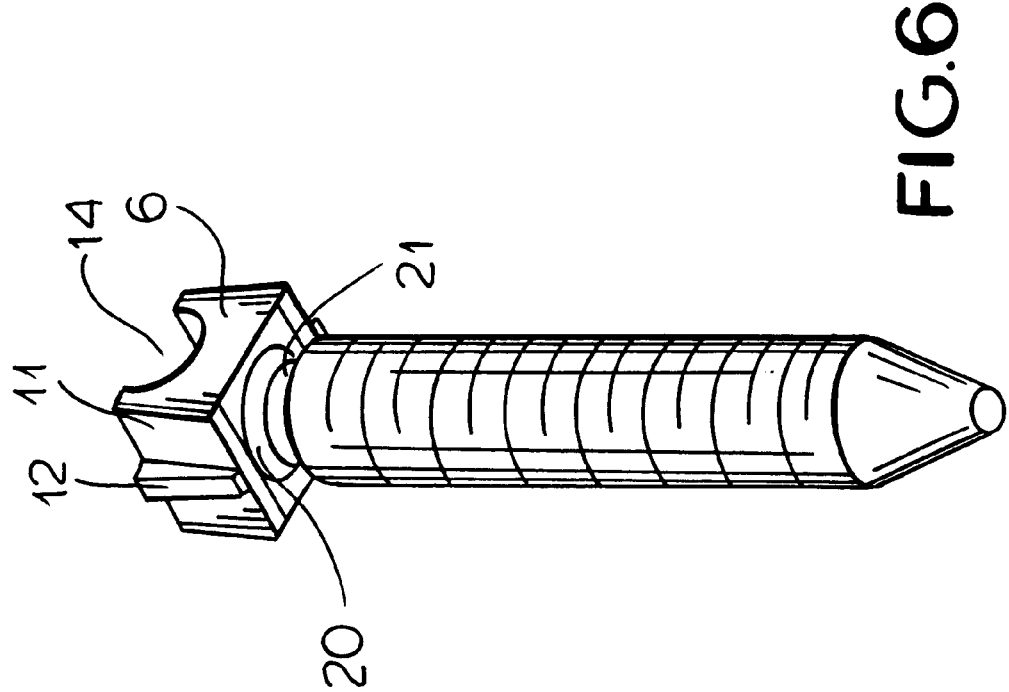
FIG. 6 is a perspective view from below of the screw with the inner cap part.
Figure 5:
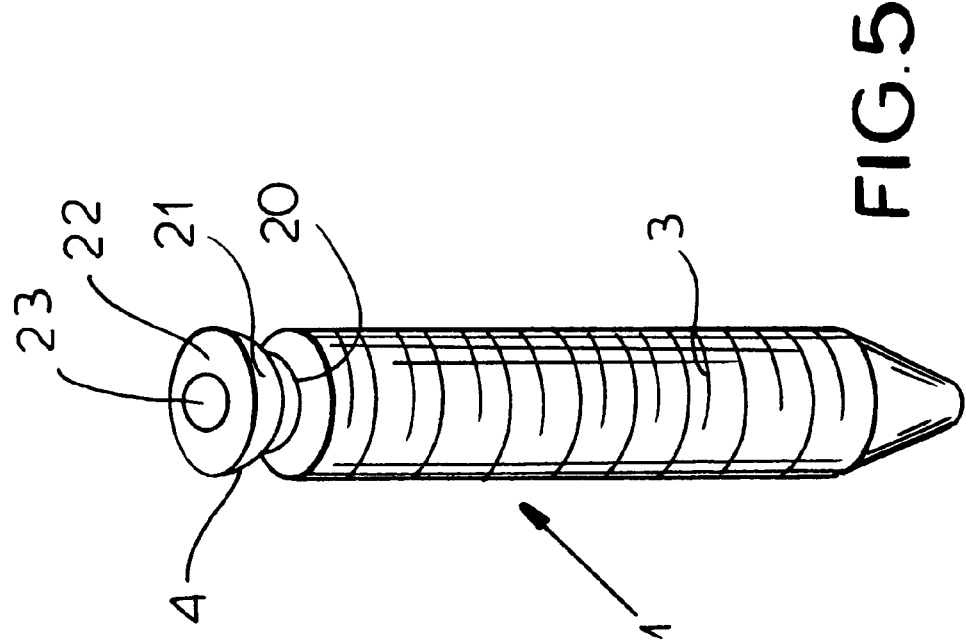
FIG. 5 is a perspective view from above of the screw.
Figure 7:
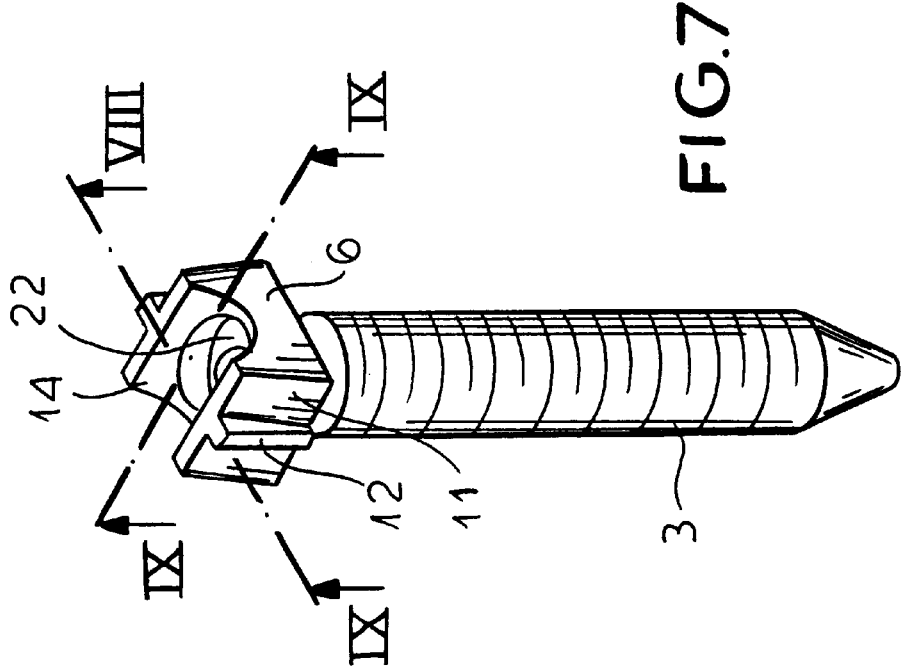
FIG. 7 is a perspective view from above of the subassembly of FIG. 6.
Figure 8:
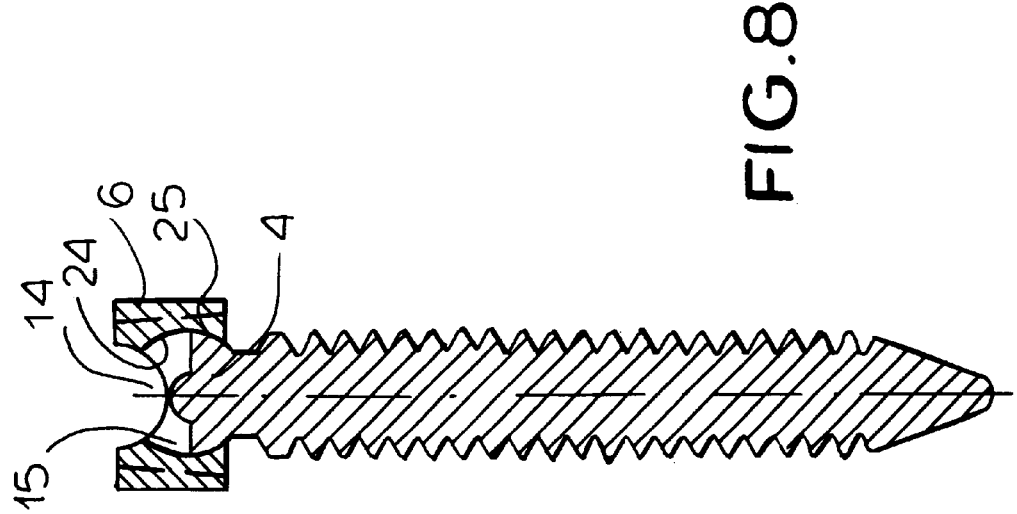

The head 4 as also shown in FIGS. 5 through 10 is defined by an inset neck groove 21 and is basically semispherical and centered on the axis A. It has a planar top surface 22 that is perpendicular to the axis A and is formed centrally thereon with a semispherical bump 23 also centered on the axis A but of a radius of curvature equal to about one third of that of the head 4 so that, in effect, the surface 22 is a planar annular land surrounding the bump 23.

The cap 5 as also shown in FIGS. 6 through 11 comprises an inner part 6 and an outer part 7. The inner part 6 has a part-spherical cavity 24 complementary to an outer surface 20 of the head 4 so that the inner part can swivel on the head 4 about a point on the axis A, and an upwardly or outwardly open part-cylindrical recess or seat half 14 complementary to the rod 2. The seat half 14 of the inner part 6 is centrally open at 15 to expose the bump 23 so that a rod 2 engaged in the seat half 14 can engage this bump 23. The surfaces of the outer and inner part are roughened at 25 where they engage each other, this roughening or profiling being sufficient to impede but not prevent swiveling of the part 6 on the head 4 about a point on the axis A.

The outer part 7 is basically U-shaped and comprises a body 8 forming a downwardly open part-cylindrical seat 16 complementary to the rod 2 and a pair of arms 9 having hook- or barb-like inner ends 10 that snap under inner edges of flat sides 11 of the inner part 6. In order to accurately align the outer part 7 on the inner part 6, the side walls 11 diverge axially downward and are each formed with a ridge 12 fittable in complementary slots 13 formed in the sides 9. Complementarily, the ridges 12 could be in the sides 9 and the grooves in the side walls 11.

Grooves 17 cut into the body 8 allow these arms 9 to be deflected elastically outward to allow the outer part 7 to be pressed down on the downwardly diverging sides 11 until the ends 10 snap under the inner edges thereof. Once thus snapped together the interfitting ridge 12 and groove 13 prevent the parts 6 and 7 from moving relative to each other parallel to the axis A' and the edges 10 snapped under the sides 11 prevent relative displacement parallel to the axis A. This part 7 is further formed with a threaded hole 18 adapted to receive a hex-head set screw 19 (FIG. 4) that can press against the rod 2 to press same against the bump 23 and pull the part 7 upward away from the part 6.

With this system the screw 1 is seated in a vertebra in the standard manner. This can be done with the inner cap part 6 attached or it can be subsequently snapped on. Then the rod 2 is laid in the recess 14 of the inner part 6 and the outer part 17 is snapped into place over it. The screw 19 is then tightened to lock the parts 1, 2, 5, and 6 together. The ability of the cap 5 to swivel about a point on the axis A allows a wide range of relative angular positions between the axes A and A'.

We claim:

1. A pedicle-screw assembly comprising:
   a screw extending along an axis and having a threaded shaft and a round head;
   an inner cap part carried on the head and swivelable on the head;
   a generally U-shaped outer cap part formed with
      a base forming with the inner cap part a seat adapted to hold an end of a distraction/stabilizing rod, and
      a pair of legs projecting parallel to the axis, flanking the cap inner part, and having ends elastically deflectable transversely away from each other to snap fit axially over the cap inner part;
   means including interengageable formations on the cap parts for blocking movement of the cap parts relative to each other transverse to the axis when the outer cap part is snap fitted over the inner cap part; and
   means on the outer cap part for fixing the rod in the seat.

2. The pedicle-screw assembly defined in claim 1 wherein the screw head has an inner region with a part-spherical outer surface and an end face lying on a plane substantially perpendicular to the screw axis.

3. The pedicle-screw assembly defined in claim 2 wherein the head is formed on the end face with a central part-spherical bump centered on the axis.

4. The pedicle-screw assembly defined in claim 1 wherein each of the legs has an outer end that hooks under an edge of the respective side of the cap inner part.

5. The pedicle-screw assembly defined in claim 1 wherein the outer cap part is formed parallel to and adjacent each leg with a groove, whereby lateral elastic deformation of the leg is increased.

6. The pedicle-screw assembly defined in claim 5 wherein the outer-cap legs and the inner cap part have confronting side faces the interengaging formations including at least one axially extending ridge on one of the faces and a complementary axially extending slot on the face confronting the one face.

7. The pedicle-screw assembly defined in claim 6 wherein the one face having the ridge is on the inner cap part.

8. The pedicle-screw assembly defined in claim 1 wherein the head and inner cap part have surfaces that engage each other and that are roughened, the fixing means being a screw threaded into the outer cap part and tightenable to pull the surfaces of the inner cap part and head axially together.

9. The pedicle-screw assembly defined in claim 1 wherein the outer and inner cap parts are formed with confronting part-cylindrical concavities forming the seat.

10. The pedicle-screw assembly defined in claim 9 wherein the screw head has an inner region with a part-spherical outer surface, an end face lying on a plane substantially perpendicular to the screw axis, and a central part-spherical bump centered on the axis on the end face, the fixing means being a screw threaded in the outer part and pressing the rod in the seat against the bump.

11. The pedicle-screw assembly defined in claim 1 wherein the screw is formed at a base of the head with an annular inset.

12. A pedicle-screw assembly comprising:
   a screw extending along an axis and having a threaded shaft and a round head;
   an inner cap part carried on the head and swivelable on the head;
   a generally U-shaped outer cap part formed with
      a base forming with the inner cap part a seat adapted to hold an end of a distraction/stabilizing rod, and
      a pair of legs projecting parallel to the axis, flanking the cap inner part, and having ends engaged in a snap fit over the cap inner part, the legs and the cap inner part having confronting side faces,
   means including an axially extending ridge on one of the side faces and a complementary axially extending slot on the other of the side faces for blocking movement of the cap parts relative to each other transverse to the axis; and
   means on the outer cap part for fixing the rod in the seat.

13. The pedicle-screw assembly defined in claim 12 wherein the screw head has an inner region with a part-spherical outer surface and an end face lying on a plane substantially perpendicular to the screw axis.

14. The pedicle-screw assembly defined in claim 13 wherein the head is formed on the end face with a central part-spherical bump centered on the axis.

15. The pedicle-screw assembly defined in claim 12 wherein each of the legs has an outer end that hooks under an edge of the respective side of the cap inner part.

16. The pedicle-screw assembly defined in claim 12 wherein the outer cap part is formed parallel to and adjacent each leg with a groove, whereby lateral elastic deformation of the leg is increased.

17. The pedicle-screw assembly defined in claim 12 wherein the one face having the ridge is on the inner cap part.

18. The pedicle-screw assembly defined in claim 12 wherein the head and inner cap part have surfaces that engage each other and that are roughened, the fixing means being a screw threaded into the outer cap part and tightenable to pull the surfaces of the inner cap part and head axially together.

19. The pedicle-screw assembly defined in claim 12 wherein the outer and inner cap parts are formed with confronting part-cylindrical concavities forming the seat.

20. The pedicle-screw assembly defined in claim 12 wherein the screw is formed at a base of the head with an annular inset.

21. A pedicle-screw assembly comprising:
   a screw extending along an axis and having a threaded shaft and a round head, the head having
      an inner region with a part-spherical outer surface,
      an end face lying on a plane substantially perpendicular to the screw axis, and
      a central part-spherical bump centered on the axis on the end face;
   an inner cap part carried on the head, swivelable on the head, and formed with a part-cylindrical concavity;
   an outer cap part formed with a part-cylindrical concavity forming with the inner-cap concavity a seat adapted to hold an end of a distraction/stabilizing rod;
   formations on the outer cap part engageable in a snap fit over the inner cap part; and
   means including a screw threaded in the outer part and pressing the rod in the seat against the bump for fixing the rod in the seat.

22. The pedicle-screw assembly defined in claim 21 wherein the screw head has an inner region with a part-spherical outer surface and an end face lying on a plane substantially perpendicular to the screw axis.

23. The pedicle-screw assembly defined in claim 21 wherein the outer cap part is generally U-shaped and formed with
   a base forming the seat and carrying the fixing means and
   a pair of legs projecting parallel to the axis, flanking the cap inner part, and having ends engaged around sides of the cap inner part.

24. The pedicle-screw assembly defined in claim 23 wherein each of the legs has an outer end that hooks under an edge of the respective side of the cap inner part.

25. The pedicle-screw assembly defined in claim 23 wherein the outer cap part is formed parallel to and adjacent each leg with a groove, whereby lateral elastic deformation of the leg is increased.

26. The pedicle-screw assembly defined in claim 21, further comprising
   means including interengaging formations on the cap parts for blocking movement of the cap parts relative to each other transverse to the axis.

27. The pedicle-screw assembly defined in claim 26 wherein the outer and inner cap surfaces have confronting side faces, the interengaging formations including at least one axially extending ridge on one of the faces and a complementary axially extending slot on the face confronting the one face.

28. The pedicle-screw assembly defined in claim 27 wherein the one face having the ridge is on the inner cap part.

29. The pedicle-screw assembly defined in claim 21 wherein the head and inner cap part have surfaces that engage each other and that are roughened, the fixing means being a screw threaded into the outer cap part and tightenable to pull the surfaces of the inner cap part and head axially together.

30. The pedicle-screw assembly defined in claim 21 wherein the screw is formed at a base of the head with an annular inset.

* * * * *